July 23, 1968 D. M. STONE Plant Pat. 2,820
MAGNOLIA TREE
Filed Nov. 23, 1966
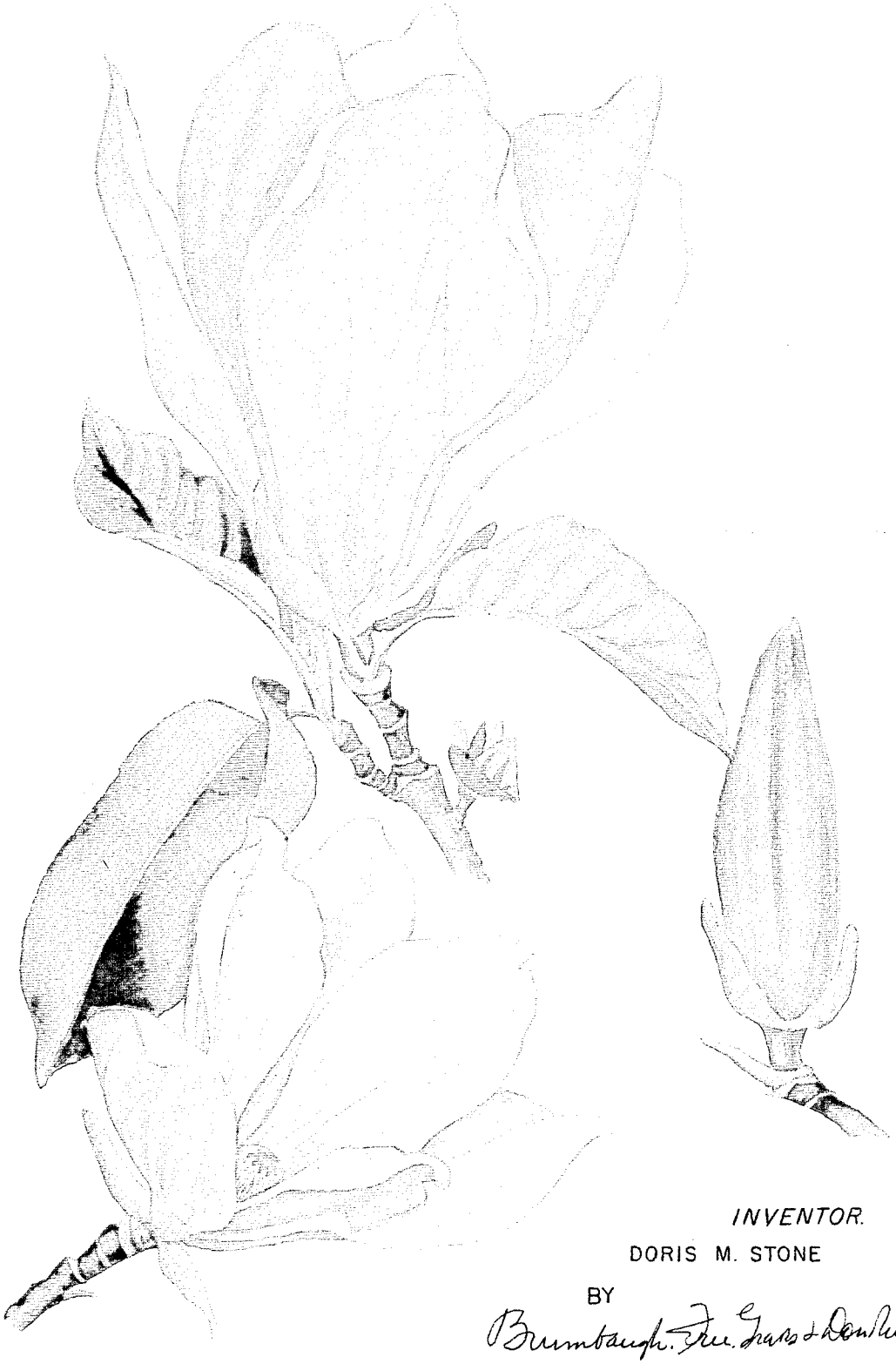
INVENTOR.
DORIS M. STONE
BY
Burnbaugh, Free, Graves & Donlevy
her ATTORNEYS.

United States Patent Office

Plant Pat. 2,820
Patented July 23, 1968

2,820
MAGNOLIA TREE

Doris M. Stone, Hastings-on-Hudson, N.Y., assignor to Brooklyn Botanic Garden of the Brooklyn Institute of Arts and Sciences, Brooklyn, N.Y., a corporation of New York Filed Nov. 23, 1966, Ser. No. 596,740
1 Claim. (Cl. Plt.—51)

The present invention relates to plant varieties involving trees of the magnolia type which exhibit distinctive and unusual colored blooms, outstanding floriferous habits, and an extended blooming period occurring later in the spring when the danger of frost damage to the flowers in cold temperate climate is past.

Varieties of magnolia trees now known either are not sufficiently hardy for cultivation in temperate climates or bloom so early in the spring that there is danger of the flowers being damaged by frost. Their bloom period is also relatively short. It is an object of this invention to provide a hardy type magnolia tree of striking appearance and beauty, having not only a prolonged bloom period occurring later in the spring, but also flowers that differ distinctly from others of the magnolia genus either in color, shape or size.

The flowers of this invention are exhibited in the accompanying drawing, which is a reproduction in color showing the blossoms.

The seedling of this new magnolia is characterized in habit as attaining a height of fifteen feet in ten years. The tree is multi-trunked, and the bark of the older branches and trunks is smooth and gray with large and conspicuous lenticels, a common quality of most magnolias. Its growth vigor is considerably in excess of other offspring of the same cross.

The vegetative buds of the tree are slender and very slightly sickle-shaped, resembling to a marked degree those of the female parent, *Magnolia acuminata*. They are from 15 to 22 mm. long. The flower buds are larger and fatter than the vegetative buds, varying from 25 to 30 mm. in length. The bud scales are covered with grayish green short sliky hairs which lie flat (appressed) against the surface of the bud scale, a characteristic shared with the female parent.

The leaves of this new tree are oval and entire with recurved edges. The apices are abruptly acuminate with triangular tips from 15 to 20 mm. long. The bases are for the most part wedge-shaped and equal, although in a few cases they are a few millimeters oblique. The leaves vary in length from 14 to 18 cm. and in width from 8.5 to 11 cm. The upper surfaces of the leaves are bright green and inconspicuously hairy while the lower surfaces, also bright green, are softly pubescent, giving them a silvery tinge. The distance between the lateral veins along the midrib is 1½ cm. on the average. The petioles are from 2 to 2½ cm. long. Twigs of the current year's growth are light chocolate brown, but become gray with age.

As in all magnolias, the flowers of the new magnolia tree occur at the ends of the branches, and flowering begins when the leaves are expanding but have not yet reached full size. The unopened flower buds are magnolia purple o30/3 suffused with tones of both lettuce green 861/3 and yellow ochre o7/3 (Robert F. Wilson's Horticultural Color Chart, 1941), a unique color among the magnolias. The open flower consists of six petals, each spatulate with a broad rounded tip, varying in length from 10.4 to 11.5 cm. and in width from 4.5 to 5.4 cm. The petals are arranged in two whorls of three petals each. The distinctive and unusual color of the flowers is due to the three shades of magenta rose, o27/3, o27/2 and o27/1, in the petals, these shades being suffused with pale orange—yellow ochre o7/2 (Robert F. Wilson's Horticultural Color Chart, 1941). The inner surface of the petals is pale pink, but this color is not of much importance because the flowers, like of the female parent, do not open widely even at maturity. The flower is approximately 9.6 cm. across at maturity, and the shape is campanulate. The stamens are pale yellow in color with pale purple bases. The pistils are also pale yellow, and the stigmas are tipped with pale purple. The pedicels are green and approximately 1 cm. long, while the sepals are three in number and measure 2.7 to 4.2 cm. in length.

The magnolia tree of the present invention originated as a seedling from several hundred crosses between the tetraploids *Magnolia acuminata* (female parent) and *Magnolia liliflora* var. *nigra* (male parent). The seeds resulting from the pollinations were collected, stratified and planted at the Brooklyn Botanic Garden, Brooklyn, N.Y. After a year's growth in a cold frame they were removed to the nursery at Kitchawan Research Station of the Brooklyn Botanic Garden, Westchester, N.Y., where the unique nature of the particular seedling was discovered when it flowered.

*Magnolia acuminata,* the female parent of this new magnolia, is a species found in the wild from New York to Georgia and west to Illinois and Arkansas. In its native region this tree attains a height of 100 feet. The leaves, which are deciduous, are scattered on the twigs. In shape they are broadly oblong to elliptic, abruptly acuminate, and from 15 to 30 cm. long. They are bright green in color and slightly pubescent on the undersurface. The flowers are globose and consist of six oblanceolate or oblong-spatulate shaped petals 4.5 to 6.5 cm. in length. The outer petals are bluish green and the inner petals are yellow. The sepals are small, green and three in number, and the andrecium and gynecium are yellow.

The male parent of this magnolia tree is a variety of the Chinese species *Magnolia liliflora* which was introduced into this country from Japan in 1861 and is called *Magnolia liliflora* var. *nigra*. This variety is a deciduous shrub 8 to 10 feet tall. The leaves are scattered on the twigs, are obovate or elliptic-ovate in shape with short acuminate or acutely acuminate tips, and are from 10 to 18 cm. long. They are dark green and sparingly pubescent above, light green beneath and finely pubescent on the veins. The large campanulate flowers are composed of seven petals which are obovate, oblong and obtuse in shape and 10.5 to 11.5 cm. in length. The petals are dark purple on the outside and lighter purple on the inside. The three small sepals are green, and the gynecium and andrecium are purple.

The magnolia tree of this invention differs from its parents primarily in its increaesd hardiness and vigor, increased bloom period, unique petal color which combines the purple tones of the male parent with the yellow pigment of the female parent, and flowers which differ distinctly in shape as well as color.

The male parent is at its northern limit of hardiness in Brooklyn and, based on observations at the Brooklyn Botanic Garden, the male parent in this geographical zone has poor growth and is far from vigorous and susceptible to winter kill. In contrast, the new magnolia grows vigorously and flowers profusely every spring at the Brooklyn Botanic Garden's nursery in northern Westchester which is in an unprotected location and exposed to wind, a much more exposed habitat than in the Brooklyn Garden.

The blooming period at the Brooklyn Botanic Garden, Brooklyn, N.Y., averages for the male parent 14 days from May 4th to 18th and for the female parent 19 days from May 12th to 31st. The new magnolia at the Kitchawan nursery at Westchester, N.Y., has bloomed on the average for 27 days from May 12th to June 9th.

The tree of the present invention was first asexually reproduced by the applicant, Doris M. Stone, at her home at Hastings-on-Hudson, N.Y., in 1963 by taking softwood cuttings late in June. The ends of the cuttings are dipped in hormone powder before being placed in a constant or intermittent mist chamber, and after six to eight weeks the rooted cuttings are put in pots.

I claim:

A new and distinct variety of late blooming magnolia tree as herein described and illustrated, characterized in that the buds are of magnolia purple suffused with tones of lettuce green and yellow ochre and the petals, arranged in two whorls of three petals each, are of shades of magenta rose suffused with pale orange.

No references cited.

ROBERT E. BAGWILL, *Primary Examiner.*